(12) United States Patent
Pickering et al.

(10) Patent No.: US 7,449,005 B2
(45) Date of Patent: Nov. 11, 2008

(54) TRACTION COLLAR AND METHOD OF USE

(75) Inventors: Will Pickering, Brooklyn, NY (US);
Lisa A. G. Tweardy, Moorestown, NJ (US); Robert M. Gorsen, McLean, VA (US); Clay A. Burns, New York, NY (US)

(73) Assignee: Ossur hf. (IE)

( * ) Notice: Subject to any disclaimer, the term of this patent is extended or adjusted under 35 U.S.C. 154(b) by 128 days.

(21) Appl. No.: 11/536,062

(22) Filed: Sep. 28, 2006

(65) Prior Publication Data
US 2007/0106194 A1    May 10, 2007

Related U.S. Application Data

(60) Provisional application No. 60/734,237, filed on Nov. 7, 2005.

(51) Int. Cl.
*A61F 5/00* (2006.01)
(52) U.S. Cl. .......................................... 602/18; 602/32
(58) Field of Classification Search ............. 602/17–19, 602/32–40
See application file for complete search history.

(56) References Cited

U.S. PATENT DOCUMENTS

| | | | |
|---|---|---|---|
| 4,166,459 A | * | 9/1979 | Nightingale ............... 602/35 |
| 4,383,523 A | | 5/1983 | Schurman |
| 4,628,913 A | | 12/1986 | Lerman |
| 4,827,915 A | | 5/1989 | Gorsen |
| 5,005,563 A | | 4/1991 | Veale |
| 5,067,483 A | * | 11/1991 | Freed ........................... 602/18 |
| 5,195,947 A | | 3/1993 | Bode |
| 5,242,377 A | | 9/1993 | Boughner et al. |
| 5,302,170 A | | 4/1994 | Tweardy |
| 5,531,669 A | | 7/1996 | Varnau |
| 5,865,773 A | | 2/1999 | Koledin |
| 5,964,722 A | | 10/1999 | Goralnik et al. |
| 6,171,273 B1 | | 1/2001 | Saunders |
| 6,267,741 B1 | | 7/2001 | Lerman |
| 6,315,746 B1 | | 11/2001 | Garth et al. |

(Continued)

FOREIGN PATENT DOCUMENTS

EP    1 738 724 A1    1/2007

(Continued)

OTHER PUBLICATIONS

The Saunders Group, Inc., "Saunders Cervical Traction, Effective Treatment for Neck Pain and Dysfunction" Product Information Brochure, 2004 and two related webpages.

(Continued)

*Primary Examiner*—Michael A. Brown
(74) *Attorney, Agent, or Firm*—Schnader Harrison Segal & Lewis LLP

(57) ABSTRACT

A traction device having an adjustable tensioning mechanism, the traction device attachable to a head support and a cervical collar. The tensioning mechanism includes a traction base, a slider slidably connected to the traction base and an adjustment mechanism to force the traction base and slider in opposite directions. One of the traction base or slider is at a fixed longitudinal position with respect to the head support and the other of the traction base or slider is at a fixed longitudinal position with respect to the cervical collar.

30 Claims, 11 Drawing Sheets

U.S. PATENT DOCUMENTS

| | | |
|---|---|---|
| 6,423,020 B1 | 7/2002 | Koledin |
| 6,468,240 B1 | 10/2002 | Saunders |
| 6,921,376 B2 | 7/2005 | Tweardy et al. |
| 2003/0078529 A1 | 4/2003 | Tweardy et al. |
| 2004/0084053 A1* | 5/2004 | Hess .......................... 128/870 |
| 2004/0204666 A1 | 10/2004 | Marsh |
| 2005/0159692 A1 | 7/2005 | Tweardy |

FOREIGN PATENT DOCUMENTS

| | | | |
|---|---|---|---|
| EP | 1738724 | * | 3/2007 |
| ES | 2 237 303 A1 | | 7/2005 |
| JP | 06-269470 | | 9/1994 |
| WO | WO 96-09802 A1 | | 4/1996 |
| WO | WO 98-43568 A1 | | 10/1998 |
| WO | WO 00-54709 A1 | | 9/2000 |
| WO | WO 2005-107658 A2 | | 11/2005 |

OTHER PUBLICATIONS

"PRONEX®" Product Information Brochure, © 2004.
Complex Cervical Traction Pronex® for Positive Outcomes © 1997.
International Search Report for PCT Patent Application No. PCT/US2006/042803, dated Jul. 24, 2007.

* cited by examiner

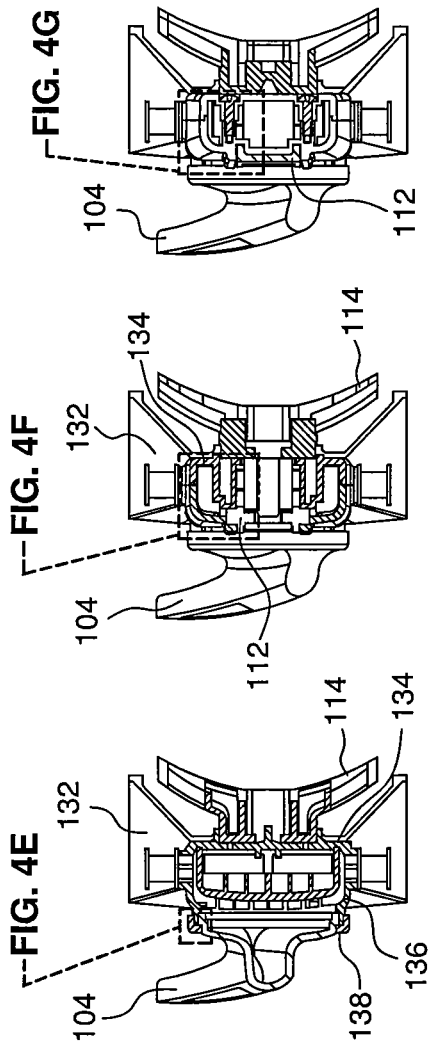
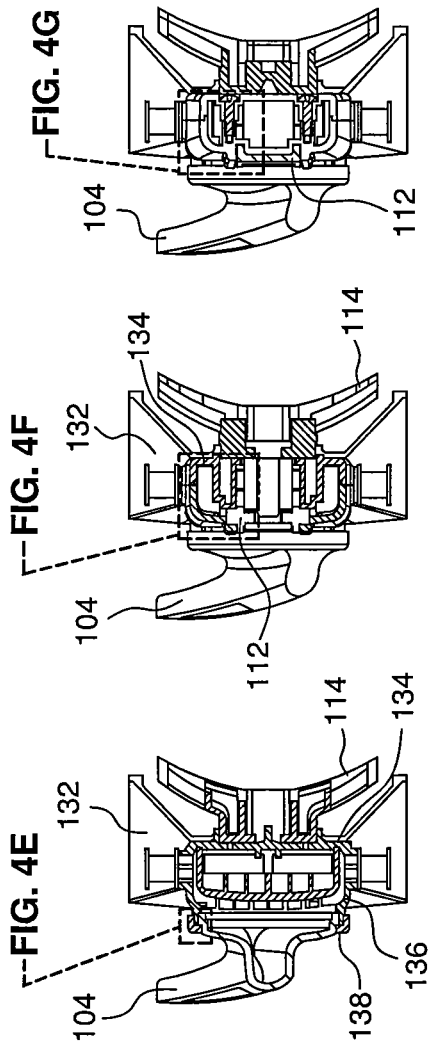
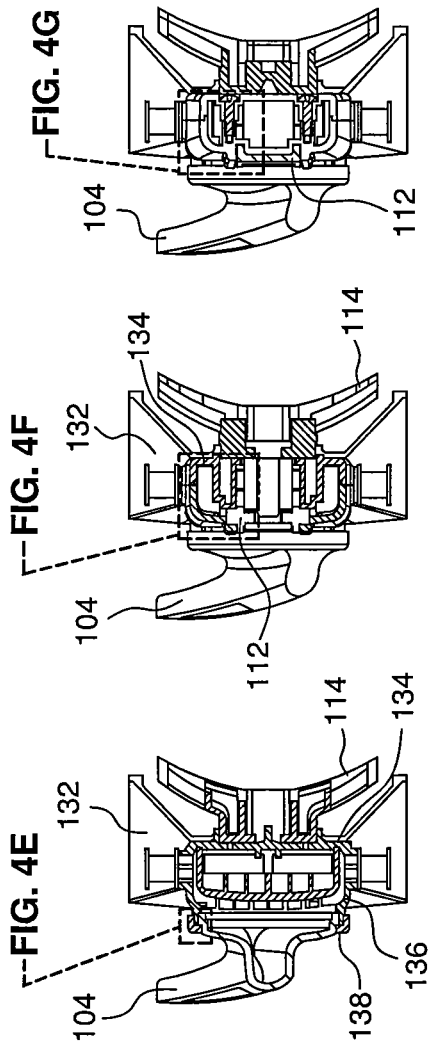
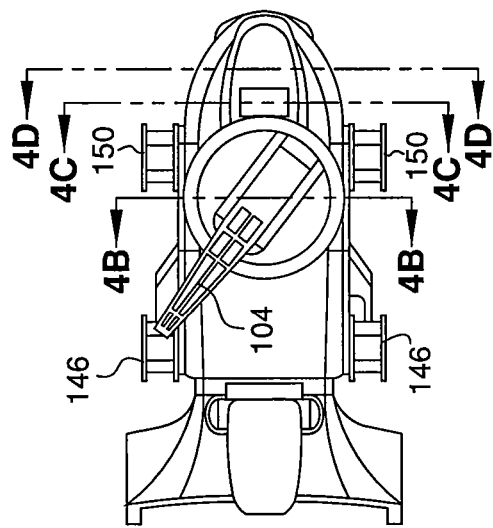
FIG. 4G
FIG. 4F
FIG. 4E
FIG. 4A
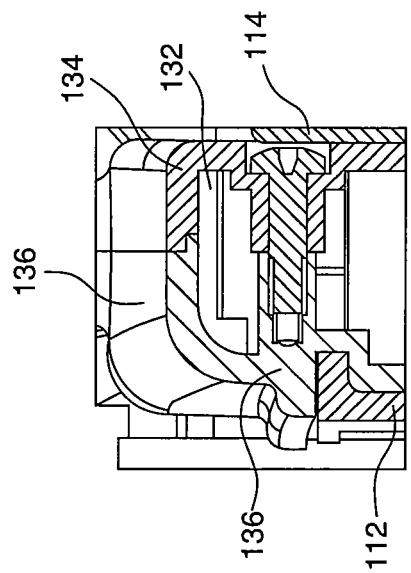
FIG. 4D
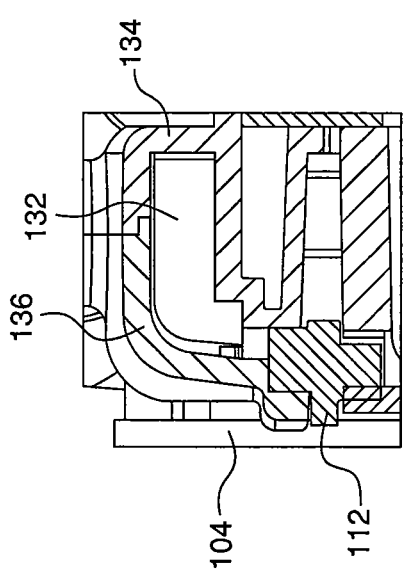
FIG. 4F
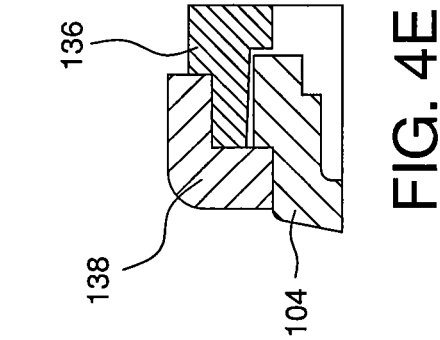
FIG. 4E

TRACTION COLLAR AND METHOD OF USE

This application is based on, and claims priority to, provisional application having Ser. No. 60/734,237 having a filing date of Nov. 7, 2005 entitled Traction Collar.

FIELD OF THE INVENTION

The invention relates to a neck brace for providing traction to the cervical spine.

BACKGROUND OF THE INVENTION

There are a number of known methods and devices to provide traction to the cervical spine. An over-the-door traction system exists wherein a patient dons a device that circles under their chin and attaches the device to an elevated point, such as the top of a door to provide traction. Such devices lack mobility, are uncomfortable and rely on patient compliance to be effective. The device is also not practical or suitable for trauma applications.

Mechanical or pneumatic devices also exist for cervical spine traction. These devices, such as the Saunders Hometrac™ and the Pronex®, also are not mobile and not suitable for trauma purposes. To use a pneumatic device the patient is typically in a prone position. Air-inflated bellows are used to create varying degrees of traction. The patient must be stationary during an extended period of time for the traction to be effective. Therefore, patient compliance can be poor.

Prior art mechanisms also do not adequately address the angle at which the head is positioned during traction. Conventional mechanisms include placing wedges with specific angles under the patient's head. Use of wedges requires patients to be stationary and provides only a limited selection of angles.

Traditional devices also include use of an inclined ramp to provide the desired angle of the head. The patient's head rests on the ramp, which is adjusted to the desired angle.

Accordingly, there is a need for a convenient, adjustable, high weight, mobile treatment system that is comfortable for the patient and is effective.

SUMMARY OF THE INVENTION

Embodiments of the invention generally include a traction device that can be used with a cervical collar with a counter-force-producing front (i.e. a force provided under the chin) or can be integral to a collar. The collar may have a dynamic or fixed support for the wearer's chin to keep the head and spine in alignment during traction. The traction device includes a traction box, which is attached to the collar and to an occipital support. Various collar types can be used with the traction device. A collar that is split into a front and back portion is particularly suitable to be used with the device.

DESCRIPTION OF THE DRAWINGS

FIGS. 4A-G depict a traction box according to an illustrative embodiment of the invention and includes details A-A, C-C, E-E, B, D and F.

DETAILED DESCRIPTION OF THE INVENTION

Embodiments of the invention include a neck brace for providing intermittent, self-contained traction to the cervical spine for the treatment of chronic neck pain, cervical spine or other medical symptoms or injuries. The device can be manufactured in a light-weight design that is particularly suitable for longitudinal traction for short-term maintenance of cervical reduction following traumatic injury or surgery. Advantageously, this dynamic traction device does not require the patient to be lying down or stationary. The traction device can easily be placed on a patient and adjusted to the desirable constant force. The amount of tension achievable may also be greater than conventional devices. The device grabs onto a patient's anatomy underneath the mastoid processes. This allows the traction to take hold so it does not slide up along the patient's head, providing the ability to impose higher weight traction than with conventional devices. Tension bands or other force-delivery components used with the traction box may also facilitate employment of higher loads than prior art traction methods.

Figure 1A:
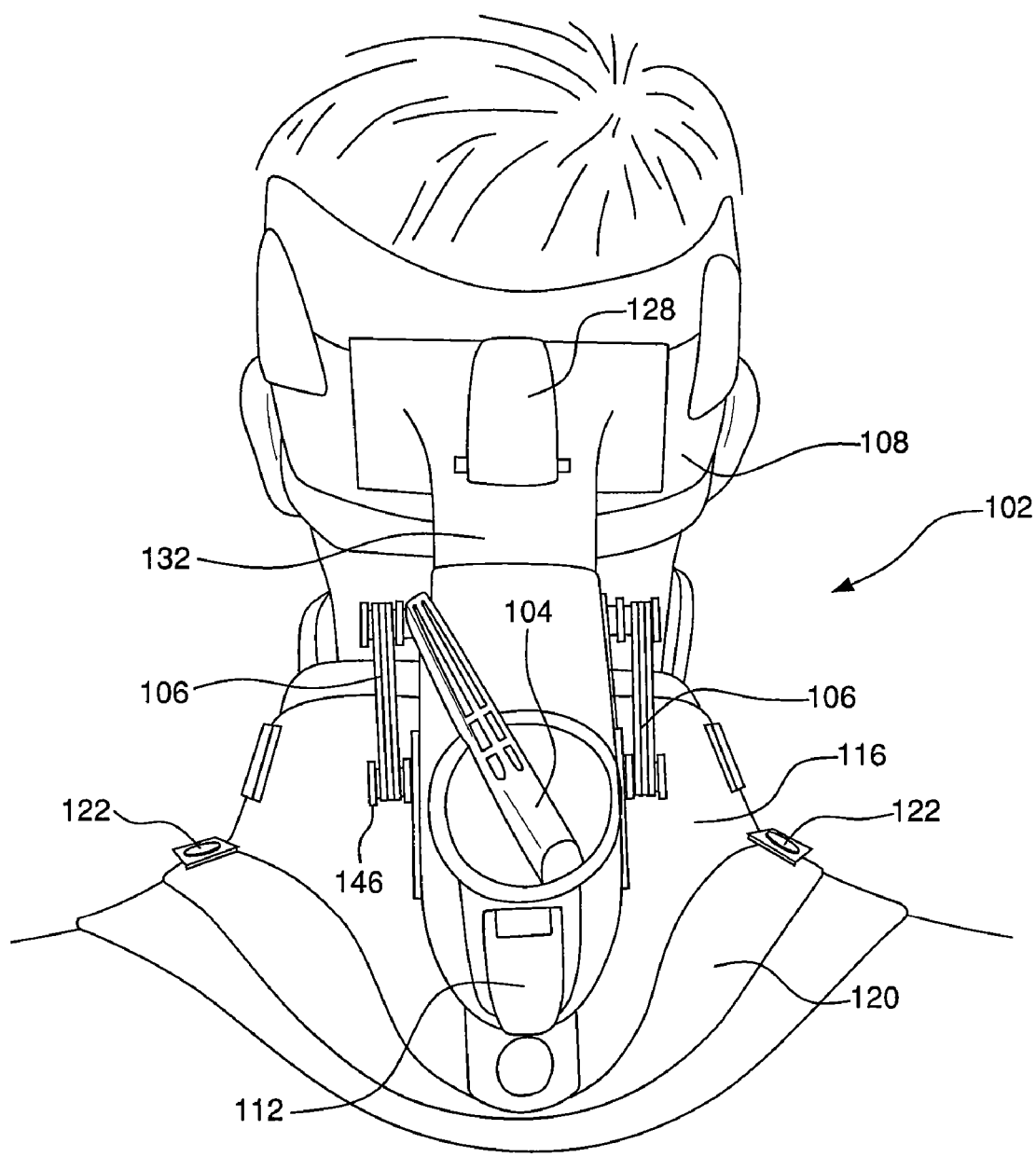
FIGS. 1A and 1B depict a traction device according to an illustrative embodiment of the invention.
Figure 1B:
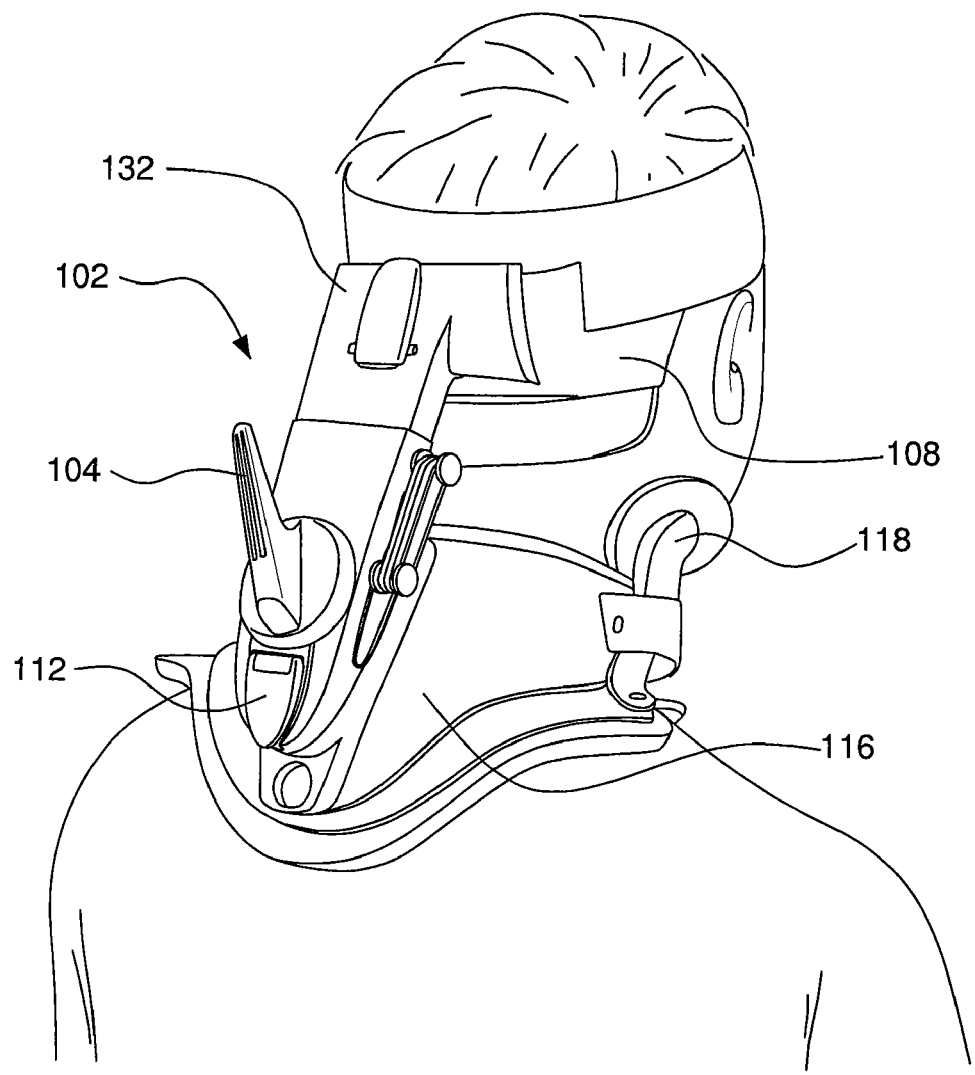

Examples of types of pain and trauma that may be treated with various embodiments of the invention include, but are not limited to:

Chronic Neck Pain resulting from:
    Facet joint syndrome
    Degenerative joint disease
    Cervical spondylosis
    Cervical nerve root compression
    Myofascial syndrome of cervical musculature Trauma
    Whiplash
    Compression Fracture
    Post-reduction fracture or dislocation
    Inter-hospital transport
    Diagnostic imaging Advantages of various embodiments of the present invention may include:
    Convenient mobile, high weight treatment
    Dynamic traction maintenance
    Comfortably supports head and neck
    Exerts prescribed force evenly and gently
    Supports normal curvature of cervical spine
    Gentle traction release
    Lightweight
    Encourages a high rate of patient compliance
    Proven effective FIGS. 1A and 1B depict a traction device according to an illustrative embodiment of the invention. Traction device includes a traction box 102 having a set release handle 104 that when rotated sets or engages force delivery components 106 to provide tension needed for traction. Force delivery components 106 are shown in FIGS. 1A and 1B as tension bands, however, other tensioning devices can be used, such as springs. The resilient members may also be mechanized or pneumatic, for example. Different strength springs or bands can be used with the inventive device to generate clinically appropriate loads.

Figure 2A:
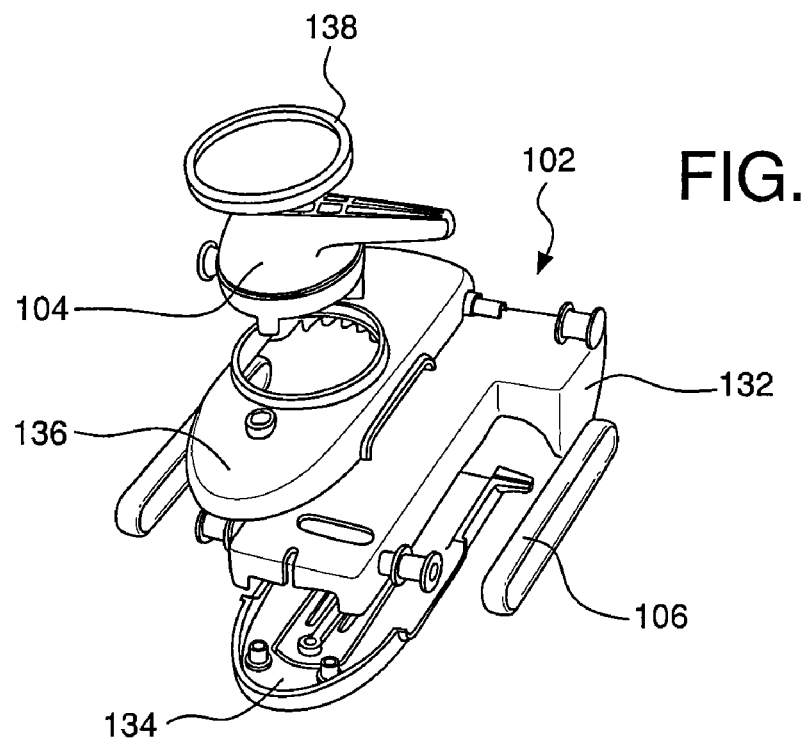
FIGS. 2A-D depict a traction box according to an illustrative embodiment of the invention.
Figure 2B:
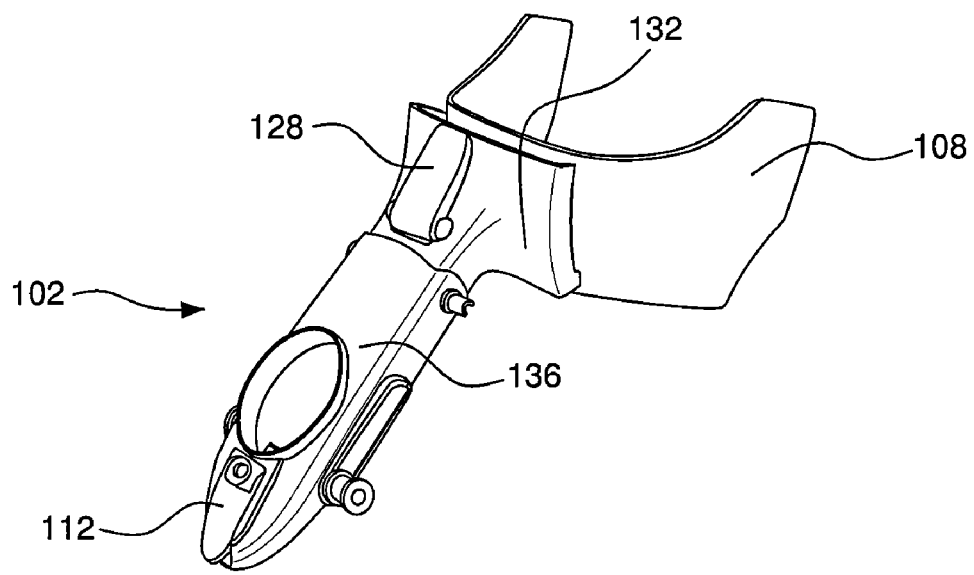
Figure 2C:
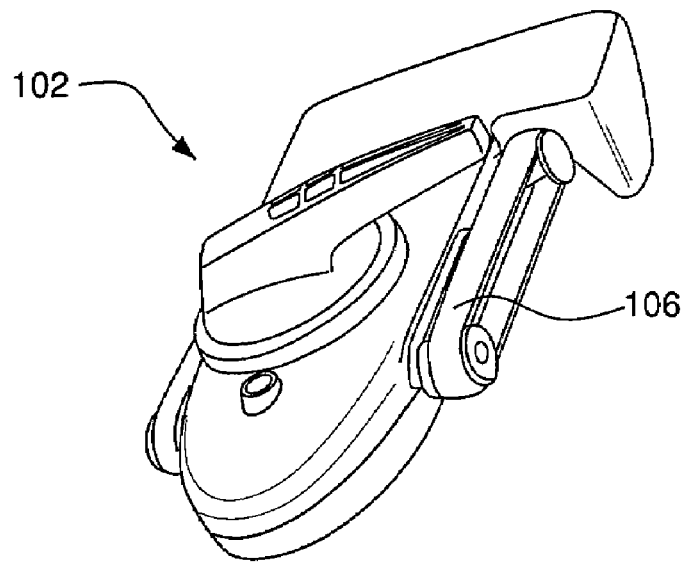
Figure 2D:
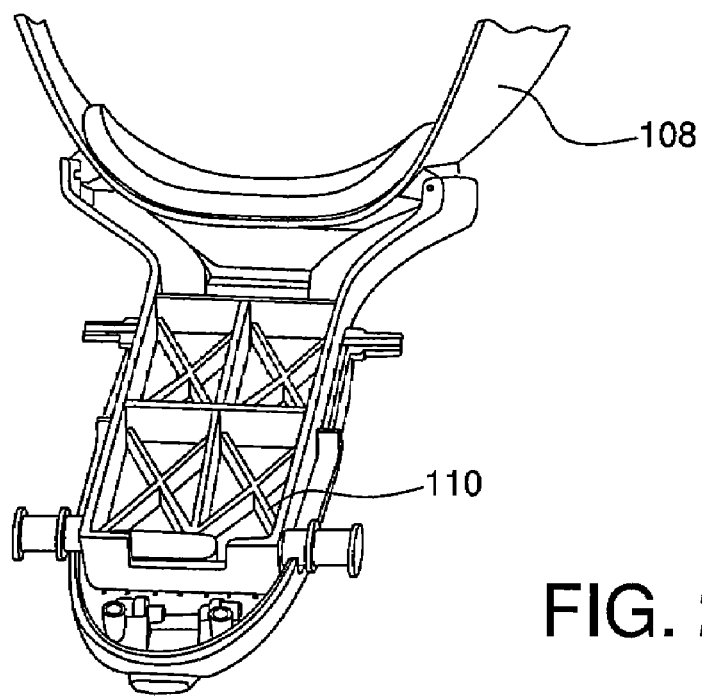

FIGS. 2A-D depict a traction box 102 and occipital support 108 according to an illustrative embodiment of the invention. FIG. 2A shows an exploded view of traction box 102. FIG. 2B shows traction box 102 attached to occipital support 108. FIG. 2C depicts traction box 102 assembled with tension bands 106 in place. FIG. 2D depicts the underside 110 of slider 132 attached to occipital support 108.

Figure 3A:
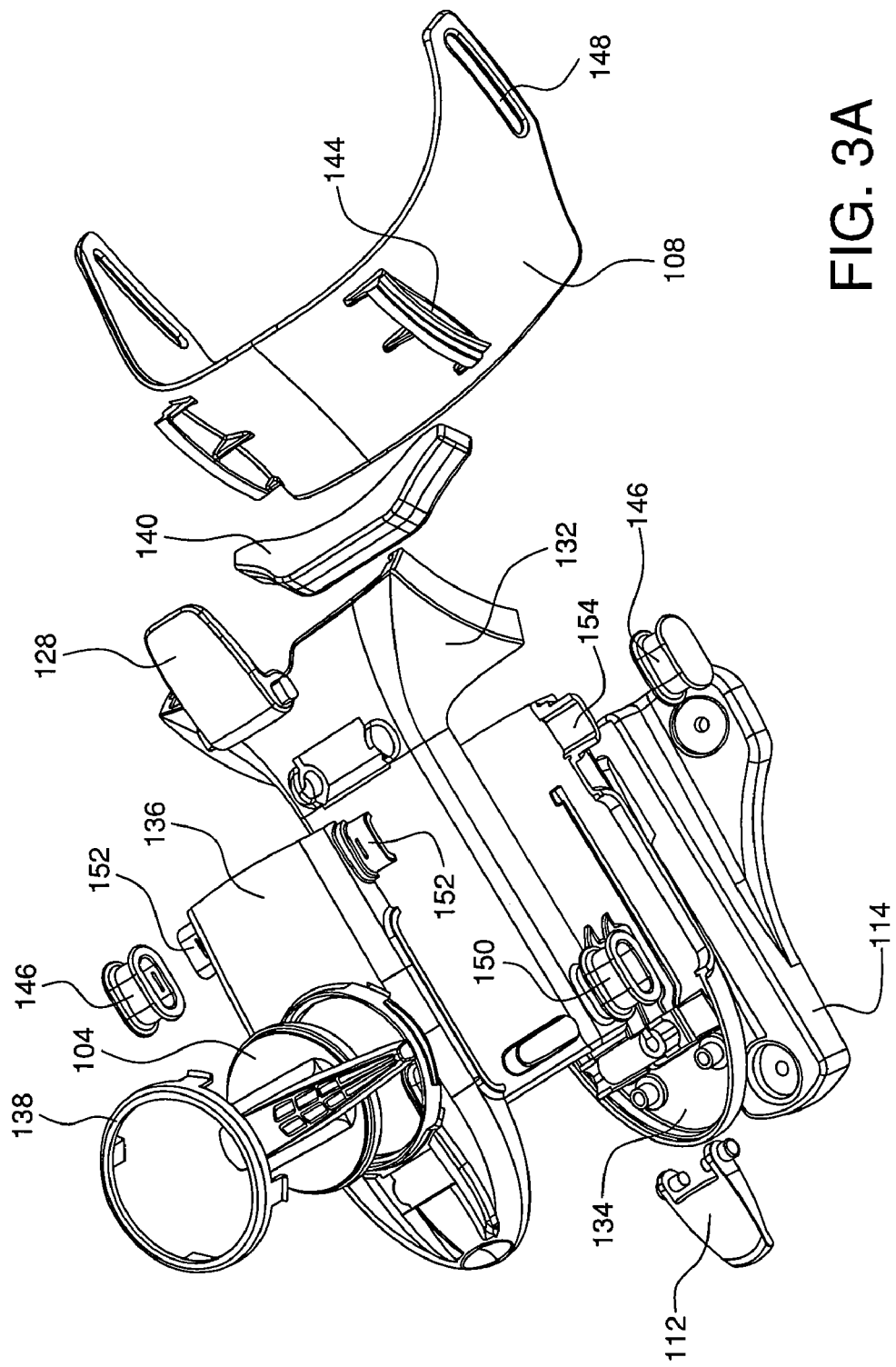
FIGS. 3A-B depict exploded views of a traction box and occipital support according to an illustrative embodiment of the present invention.
Figure 3B:
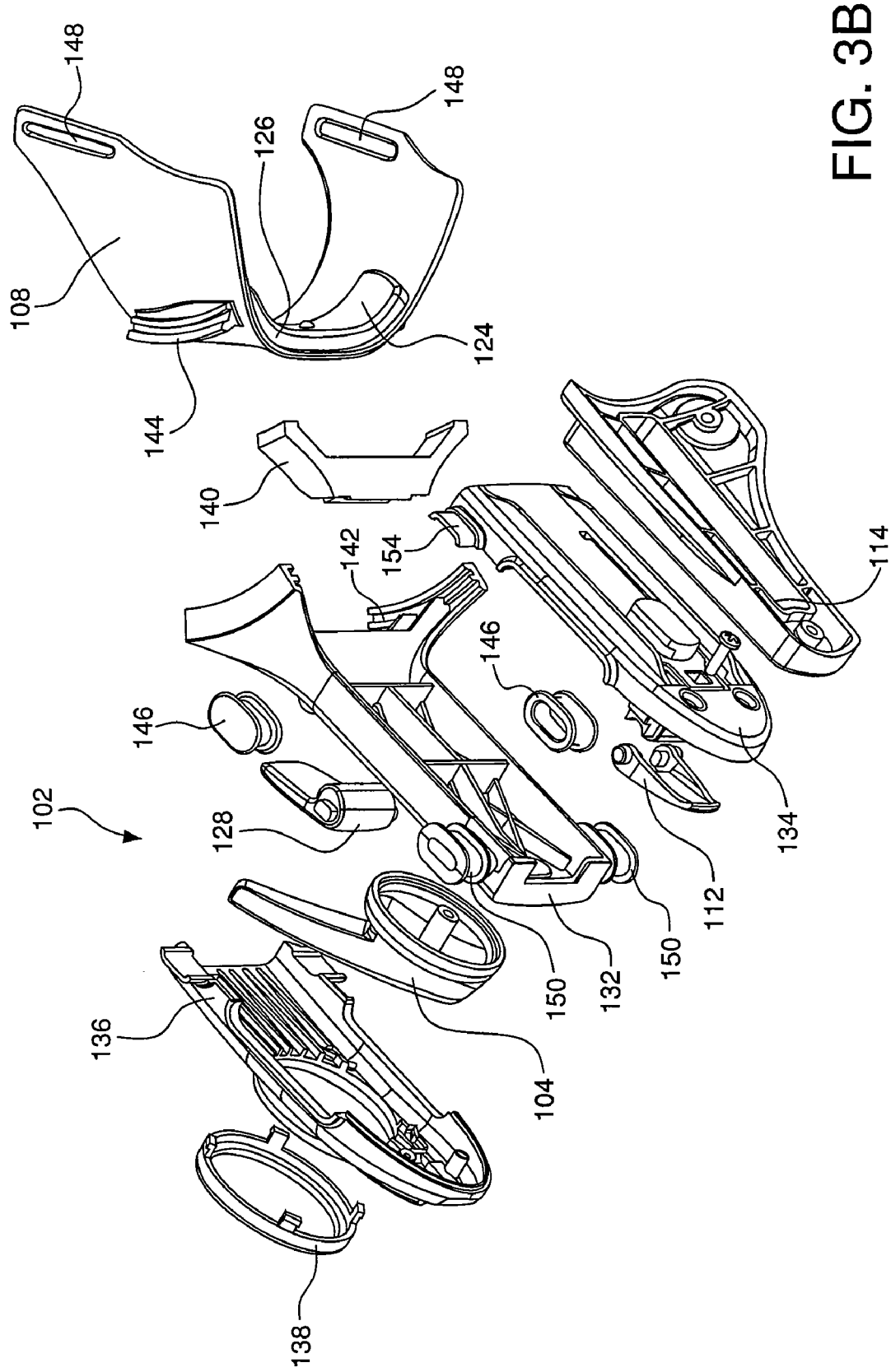
Figure 5A:
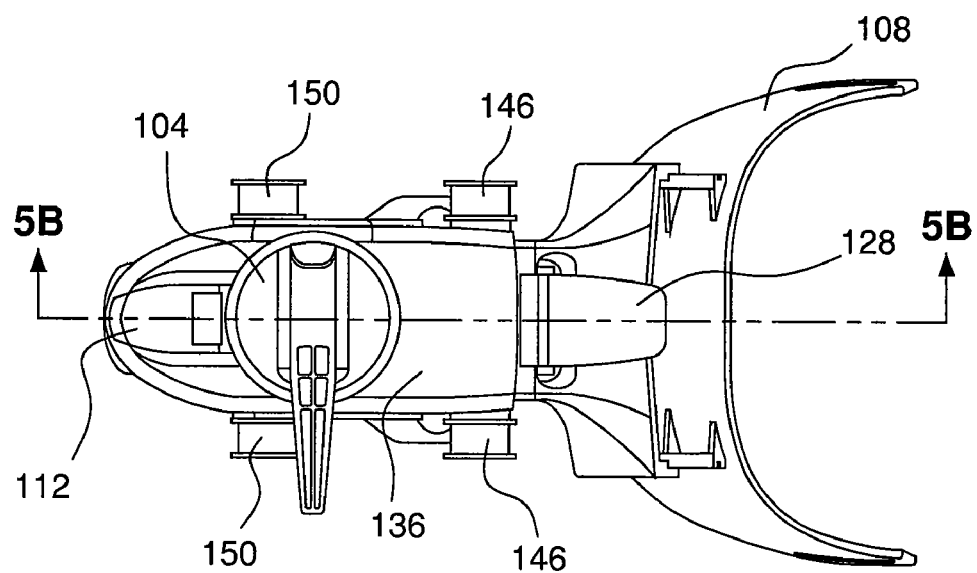
FIGS. 5A-B depict a traction box according to an illustrative embodiment of the invention and includes detail A-A.
Figure 5B:
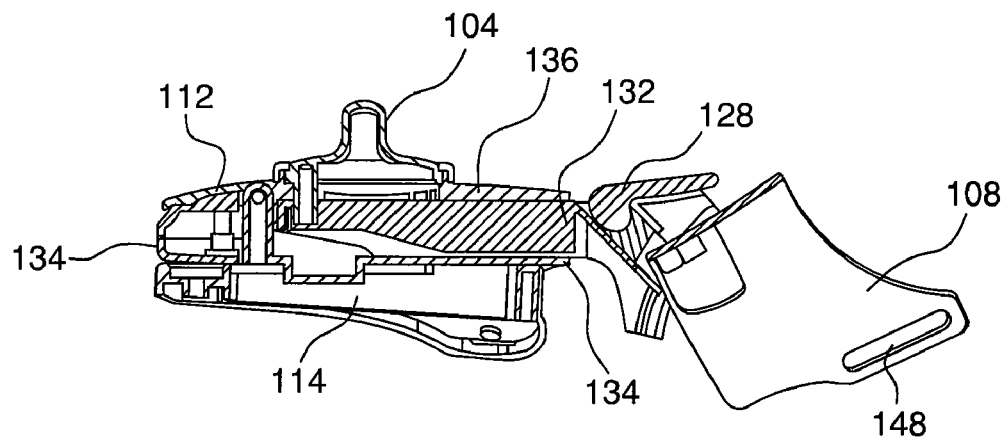

FIG. 3A is an exploded top view of a traction box 102 and occipital support 108 according to an illustrative embodiment of the present invention. FIG. 3B is an exploded bottom view of the same embodiment. FIGS. 4A-G, 5A-B and 6A-B depict traction box 102 and cross sectional details according to an illustrative embodiment of the invention. This embodiment will now be described in further detail.

Traction base 134 is sandwiched between height tract 114 and slider 132 so that slider 132 can be slid longitudinally along height tract 114 to increase or decrease the length of the traction device. By adjusting the longitudinal distance, the device can be fitted to different size patients. Once the traction device is configured to the desired height, a height lock 112 can be employed to maintain the distance. Other mechanisms can be used to provide the longitudinal adjustment, such as a ratchet mechanism, or one in which tabs or buttons are depressed to allow sliding of the component.

Traction cover 136 fits over slider 132 and connects to traction base 134. Once connected, extensions 152 on cover 136 align with extensions 154 on traction base 134 to form a shaft onto which barrels 146 are disposed. Force-delivery components, such as bands 106, are then stretched around barrels 150 and 146. This imparts a force on slider 132 toward occipital support 108 and on the base/cover combination toward collar 116, effectively creating a traction mechanism. It is noted, that although part 134 is referred to as a "base," it is not necessarily the bottom most part. The key is that two parts move in opposite directions to one another to create a traction force.

Figure 6A:
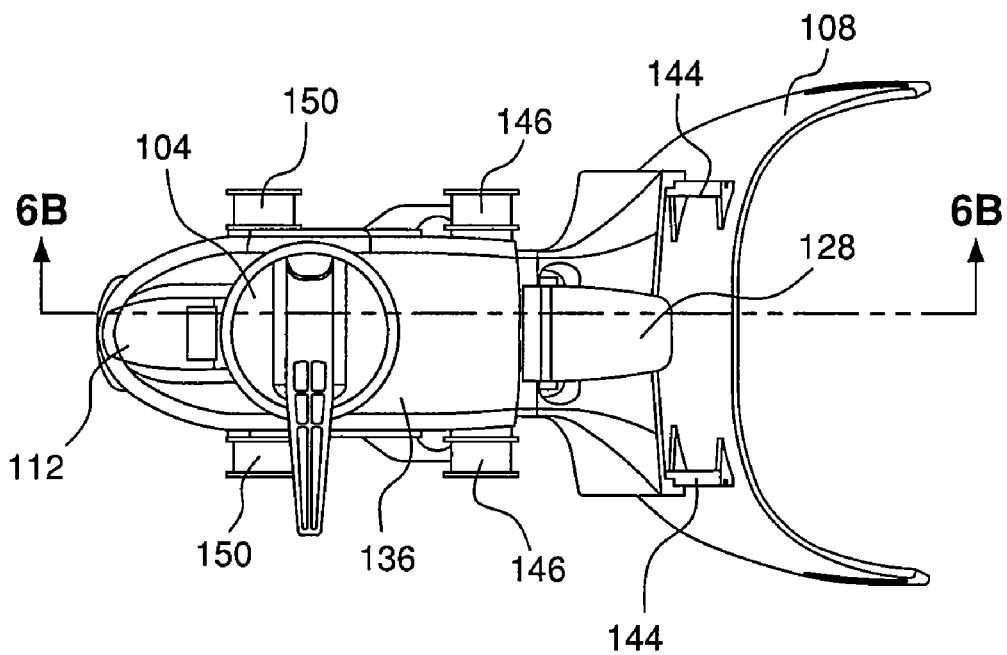
FIGS. 6A-B depict a traction box according to an illustrative embodiment of the invention and includes detail B-B.
Figure 6B:
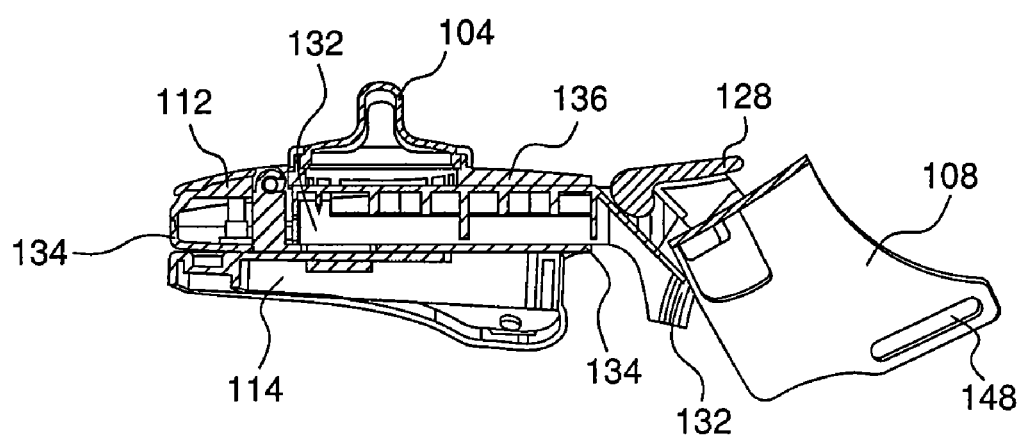

A handle retainer 138 secures handle 104 to traction box 102. Traction box 102 is further secured to occipital support 108. In this particular embodiment, slider 132 has channels 142 (as seen in FIG. 3), into which protrusions 144 (as seen in FIGS. 3 and 6A) fit. Mastoid lock transfer 140 fits within slider 132, and is functionally engaged with mastoid angle lock 128 to allow traction box 102 to be angled with respect to occipital support 108. Straps (not shown) are disposed through openings 148 and around a patient's head to secure the traction device to the wearer.

The particular embodiment of the invention shown in the figures includes a handle 104 for dialing in the desired tension. Advantageously, adjustments can be made while the device is on the wearer and with a single adjustment that disperses the tension relatively uniformly to the desired location on the head. Common prior art mechanisms have separate tensioning devices for each side of the head. It is however, possible to employ more than one traction box on a collar and apply different degrees of tension or different angles if desired. The adjustment mechanism in this embodiment is fully contained on the traction box so there are no lines, hoses, etc. that can be caught on objects or inadvertently disconnected as are present in prior art devices. This can be an important feature for a device that can be used while the patient is mobile.

Illustrative fitting instructions are as follows: The traction box 102 is tensioned by rotating handle 104 clockwise until it is loaded and locked. Height lock 112 is opened and the traction box is slid to the lowest position on height track 114. A cervical collar 116 (shown in FIGS. 1A and 1B) is selected that will appropriately fit the patient. A collar front 118 is put on the patient, preferably using Velcro® straps. A collar back 120, with traction box 102 integral or attached thereto, is then placed on the patient so the Velcro® tabs of the front and back collar portions 118, 120 are aligned. (It is noted that the traction box can be detachable from the collar.) The shoulder flanges 122 of collar 116 should be resting securely on the patient's shoulders, and the front and back collar portions 118, 120 should be secure around the patient's neck. Traction box 102 is then slid up on height track 114 until lower pads 124, 126 of occipital cradle 108 are contacting the patient's head at the mastoid process. Mastoid angle lock 128 is then opened and the angle of occipital cradle 108 is adjusted so that it is cupping the mastoid process. A Velcro® strap may then be tightened around the patient's head pulling it around the patient's head and affixing the strap to itself. Traction can then be applied by rotating handle 104. Although Velcro® straps are shown, other strap types or fastening mechanisms can be used such as elastic components or non-Velcro® straps.

Figure 7:
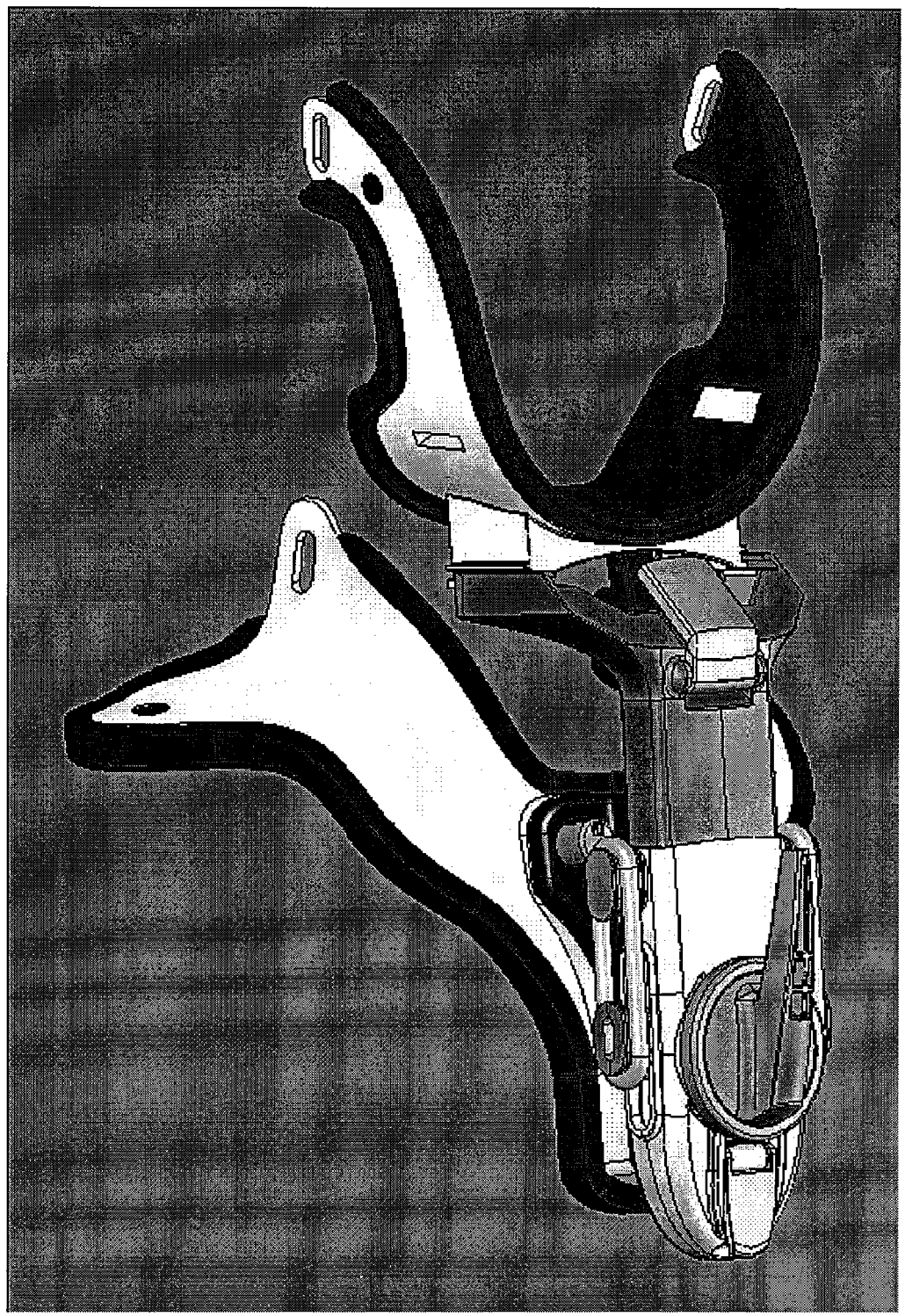
FIG. 7 depicts a traction collar according to a further illustrative embodiment of the invention.

FIG. 7 depicts a traction collar according to a further illustrative embodiment of the invention. This embodiment differs from the embodiment shown in the previously described figures, for example in the vicinity of the interface of the occipital support and the traction device.

Figure 8:
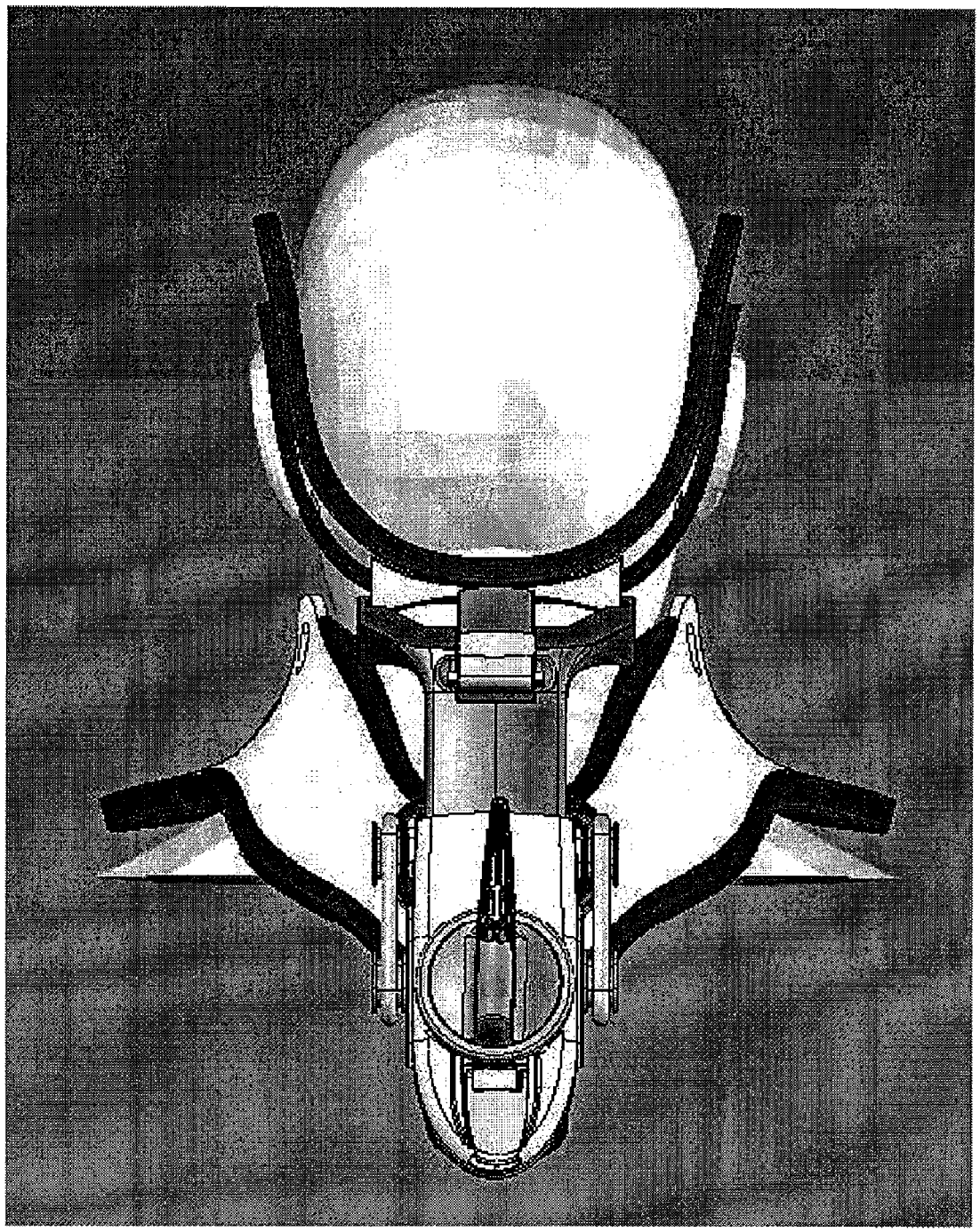
FIG. 8 depicts a traction collar positioned on a patient according to an illustrative embodiment of the invention.

FIG. 8 depicts a traction collar positioned on a patient according to an illustrative embodiment of the invention.

The invention may be embodied in a variety of ways, for example, a system, method or device. The invention includes the traction box by itself and incorporated into a cervical collar, with or without a counterforce-producing anterior collar.

While the invention has been described by illustrative embodiments, additional advantages and modifications will occur to those skilled in the art. Therefore, the invention in its broader aspects is not limited to specific details shown and described herein. Modifications, for example, to the type of force-delivery component, adjustment mechanism, and the collar design with which the traction device is used, may be made without departing from the spirit and scope of the invention. Accordingly, it is intended that the invention not be limited to the specific illustrative embodiments, but be interpreted within the full spirit and scope of the appended claims and their equivalents.

The invention claimed is:

1. A traction device comprising:
    a head support;
    a traction box connected to the head support, configured to be attached to a cervical collar, and having an adjustable tensioning mechanism, the tensioning mechanism comprising:
    a traction base;
    a slider slidably connected to the traction base;
    an adjustment mechanism to force the traction base and slider in opposite directions, the adjustment mechanism having one or more force-delivery components;
    wherein one of the traction base or slider is at a fixed longitudinal position with respect to the head support and the other of the traction base or slider is at a fixed longitudinal position with respect to the cervical collar, such that the traction box provides a force to essentially longitudinally displace the head support from the cervical collar
    and wherein the traction device, when attached to a cervical collar, will remain functionally in place when a wearer is mobile.

2. The traction device of claim 1 wherein the tensioning mechanism comprises;

force-delivery components in the form of one or more resilient members wherein a first end of a resilient member is connected to the slider and the second end of the resilient member is connected to the traction base; and an adjustment component functionally connected to the traction box to longitudinally vary the position of the slider with respect to the traction base.

3. The traction device of claim 2 wherein the resilient members are elastic bands.

4. The traction device of claim 2 wherein the resilient members are springs.

5. The traction device of claim 2 wherein the resilient members are pneumatic.

6. The traction device of claim 2 wherein the resilient members are mechanized.

7. The traction device of claim 2 wherein the adjustment component is a single rotatable component, rotatable with respect to the traction box.

8. The traction device of claim 1 further comprising a height track functionally connected to the traction box to enable the longitudinal distance between the head support and the cervical collar to be adjusted.

9. The traction device of claim 8 further comprising a height lock mechanism to maintain the longitudinal distance between the head support and the cervical collar.

10. The traction device of claim 1 further comprising an angle adjustment mechanism to adjust the angle of the traction box with respect to the head support.

11. The traction device of claim 1 further comprising an angle adjustment mechanism to adjust the angle of the traction box with respect to the cervical collar.

12. A cervical collar having a traction device according to claim 1.

13. A method of providing traction to an individual comprising:
    providing a cervical collar having a traction device according to claim 1 functionally connected thereto;
    fitting the cervical collar to the individual;
    fitting the head support to the individual; and
    adjusting the tensioning mechanism to provide a desired amount of traction force.

14. The method of claim 13 wherein the traction device includes an angle adjustment mechanism, the method further comprising:
    adjusting the angle between the traction box and the head support using the angle adjustment mechanism.

15. The method of claim 14 further comprising locking the traction device to the adjusted angle.

16. The method of claim 13 wherein the traction device includes an angle adjustment mechanism, the method further comprising:
    adjusting the angle between the traction box and the cervical collar using the angle adjustment mechanism.

17. The method of claim 16 further comprising locking the traction box to the adjusted angle.

18. The method of claim 13 wherein the traction device comprises a height track functionally connected to the traction box, the method further comprising:
    adjusting the longitudinal distance between the head support and the cervical collar using the height tract.

19. The method of claim 18 further comprising locking the height track position in place to maintain the longitudinal distance between the head support and the cervical collar.

20. A traction device comprising:
    a head support;
    a traction box connected to the head support, and having an adjustable tensioning mechanism;
    the traction box configured to be further attached to a cervical collar;
    the tensioning mechanism having:
        a traction base;
        a slider slidably connected to the traction base;
        one or more resilient members wherein a first end of a resilient member is connected to the slider and the second end of the resilient member is connected to the traction base; and
        an adjustment mechanism to force the traction base and slider in opposite directions, the adjustment mechanism having an adjustment component functionally connected to the traction box to longitudinally vary the position of the slider with respect to the traction base;
    wherein one of the traction base or slider is at a fixed longitudinal position with respect to the head support and the other of the traction base or slider is at a fixed longitudinal position with respect to the cervical collar.

21. The traction device of claim 20 wherein the resilient members are elastic bands.

22. The traction device of claim 20 wherein the resilient members are springs.

23. The traction device of claim 20 wherein the resilient members are pneumatic.

24. The traction device of claim 20 wherein the resilient members are mechanized.

25. The traction device of claim 20 wherein the adjustment component is a single rotatable component, rotatable with respect to the traction box.

26. The traction device of claim 20 further comprising a height track functionally connected to the traction box to enable the longitudinal distance between the head support and the cervical collar to be adjusted.

27. The traction device of claim 20 further comprising a height lock mechanism to maintain the longitudinal distance between the head support and the cervical collar.

28. The traction device of claim 20 further comprising an angle adjustment mechanism to adjust the angle of the traction box with respect to the head support.

29. The traction device of claim 20 further comprising an angle adjustment mechanism to adjust the angle of the traction box with respect to the cervical collar.

30. A cervical collar having a traction device according to claim 20.

* * * * *

UNITED STATES PATENT AND TRADEMARK OFFICE
CERTIFICATE OF CORRECTION

PATENT NO. : 7,449,005 B2 Page 1 of 1
APPLICATION NO. : 11/536062
DATED : November 11, 2008
INVENTOR(S) : Pickering et al.

It is certified that error appears in the above-identified patent and that said Letters Patent is hereby corrected as shown below:

Title page, item (73) Assignee, change "(IE)" to --(IS)--.

On page 2 of the title page, first column, line 13, under FOREIGN PATENT DOCUMENTS, change "3/2007" to --1/2007--.

Signed and Sealed this

Twentieth Day of January, 2009

JON W. DUDAS
*Director of the United States Patent and Trademark Office*